United States Patent [19]

Iwaki et al.

[11] Patent Number: 5,585,474
[45] Date of Patent: Dec. 17, 1996

[54] DNA ENCODING PROTEIN POSSESSING METASTASIS-INHIBITORY ACTIVITY

[75] Inventors: Kanso Iwaki; Tsunetaka Ohta; Masahi Kurimoto, all of Okayama, Japan

[73] Assignee: Kabushiki Kaisha Hayashibara Seibutsu Kagaku Kenkyujo, Okayama, Japan

[21] Appl. No.: 555,860

[22] Filed: Nov. 13, 1995

Related U.S. Application Data

[62] Division of Ser. No. 127,278, Sep. 27, 1993, Pat. No. 5,498,697.

[30] Foreign Application Priority Data

Sep. 28, 1992 [JP] Japan .................. 4-281136

[51] Int. Cl.⁶ .............. C07H 19/00; C07H 21/00; C07K 1/00; C07K 14/00
[52] U.S. Cl. .............. 536/22.1; 424/577; 435/227; 530/350; 536/23.1; 536/23.2; 536/23.5
[58] Field of Search .................. 536/22.1, 23.1, 536/23.2, 23.5; 424/577; 435/227; 530/350

[56] References Cited

U.S. PATENT DOCUMENTS 5,126,148  6/1992  Kurimoto et al. .............. 424/577

FOREIGN PATENT DOCUMENTS

| 0149751 | 7/1985 | European Pat. Off. . |
| 0401997 | 12/1990 | European Pat. Off. . |
| 2125048 | 2/1984 | United Kingdom . |

OTHER PUBLICATIONS

Jakob et al, Molecular Cloning and Sequence Analysis of DNA's . . . Aminoacylase, Biological Chemistry, vol. 372, p. 684, 1991.

Cook et al, Sequence and Expression Analysis of a Chromosome . . . Cancer, J. Biol. Chem. vol. 268, pp. 17010–17017, 1993.

Y. E. Miller et al, Human Aminoacylase–1: Cloning, Regional Assignment . . . Chromosome 18, Genomics, vol. 8, pp. 149–154, 1990.

Y. Naomoto et al, Journal of Cancer Research and Clinical Oncology, vol. 113, 1987, pp. 544–549.

U. K. Laemmli, Nature, vol. 227, 1970, pp. 680–685.

J. Sambrook et al, Molecular Cloning: A Laboratory Manual, Cold Spring Harbor Laboratory Press, 1989, Chapter 8, "Construction and Analysis of cDNA Laboratories", pp. 8.2–8.86.

Miller et al., "Human Aminoacylase–1: Cloning, Regional Assignment to Distal Chromosome 3p21.1, and identification of a Cross–Hybridizing Sequence on Chromosome 18", Genomics 8, pp. 149–154.

*Primary Examiner*—Robert A. Wax
*Assistant Examiner*—Hyosuk Kim
*Attorney, Agent, or Firm*—Browdy and Neimark

[57] ABSTRACT

Disclosed is a novel protein which has a molecular weight of 45,000±5,000 and pI 5.7±0.5 and exhibits cancer metastasis-inhibitory activity. The protein can be prepared by culturing human cells, animal cells and microorganisms capable of producing the protein in a nutrient culture medium while stimulating them with an inducer such as Bacille Calmette-Guérin and lipopolysaccharide.

2 Claims, No Drawings

DNA ENCODING PROTEIN POSSESSING METASTASIS-INHIBITORY ACTIVITY

This is a division of parent application Ser. No. 08/127,278 filed Sep. 27, 1993, now U.S. Pat. No. 5,498,697.

BACKGROUND OF THE INVENTION

1. Field of the Invention

The present invention relates to a novel protein, and a DNA coding said protein, as well as to the preparation of said protein.

2. Description of the Prior Art

Nowadays, the treatment of cancers is mainly attained by surgical operations, chemotherapies and radiotherapies. Although most of cancers may be cured by such a treatment, a part of viable cancer cells remaining after such a treatment may be scattered throughout the body of a cancer patient, and may cause a more serious cancer-metastasis and even shorten the patient's life span. If the metastasis of cancers can be inhibited, cancer patients's pain would be relieved, and their life spans would be extended much more. Therefore, the development of agents which effectively inhibit the metastasis of cancers has been in a great demand. In general, the metastasis of cancers, however, has been considered to occur via a complicated process, and this hinders the realization of satisfiable cancer metastasis-inhibitory agents.

Although a variety of proteins possessing cancer metastasis-inhibitory activity were reported, the present protein absolutely differs from them. Examples of such a conventional protein are interferons and interleukin 2 which have been reported to have cancer metastasis-inhibitory activity. The present protein clearly differs from such a conventional protein in molecular weight and amino acid sequence. None of conventional proteins have not yet been realized as a cancer metastasis-inhibitory agent. In Japanese Patent Laid-Open No.308,799/90, a cancer metastasis-inhibitory factor produced by cells derived from human hematopoietic tissues is reported and its structure and physicochemical properties are, however, far from substantial elucidation because the description in the patent is vague and it only teaches the molecular weight ranging 10,000–450,000.

OBJECTS OF THE INVENTION

One object of the present invention is to provide a novel protein which effectively inhibits the metastasis of cancers.

Another object of the invention is to provide a DNA coding said protein.

Further object of the invention is to provide the preparation of said protein.

SUMMARY OF THE INVENTION

In order to attain the aforesaid objects, the present inventors studied substances which inhibit the metastasis of cancers. The present inventors continued studies in order to obtain a novel cancer metastasis-inhibitory substance, and, as a result eventually found cancer metastasis-inhibitory activity in a culture supernatant of HPB-MLT cell (FERM BP-2430), an established cell line derived from human T-cell leukemia, which had been stimulated in a nutrient culture medium with BCG and LPS. The present inventors revealed that the entity of the activity is a protein having the following physicochemical properties:

(1) Molecular weight 45,000±5,000;

(2) Isoelectric point pI=5.7±0.5;

(3) Partial amino acid sequence

Possessing a partial amino acid sequence of Asp-Ser-Glu-Gly-Tyr-Ile-Tyr-Ala-Arg-Gly-Ala-Gln-Asp-Met-Lys (SEQ ID No: 1) or Glu-His-Trp-Ser-His-Asp-Pro-Phe-Glu (SEQ ID NO:2);

(4) Solubility in solvent

Soluble in water, physiological saline and phosphate buffer;

(5) Biological activity

Exhibiting a metastasis-inhibitory activity on RPMI 4788 cell (FERM BP-2429), an established cell line derived from human colon cancer; and (6) Stability Inactivated in water at pH 7.2 and 100° C. for 30 minutes. Stable in water at pH 7.2 and 4° C. for one month.

DETAILED DESCRIPTION OF THE INVENTION

The present inventors isolated a protein possessing cancer metastasis-inhibitory activity from a culture of HPB-MLT cell (FERM BP-2430) stimulated with BCG and LPS. The present inventors revealed the physicochemical properties of said protein and found that it has the amino acid sequence as shown in Chemical formula 1. (SEQ ID NO: 4) The wording "substantially has the amino acid sequence as shown in Chemical formula 1" as referred to in the invention means that it should not be restricted to that as shown in Chemical formula 1 and shall include all the homologous variants thereof. In other words, the present invention includes any protein having a partial amino acid sequence in the amino acid sequence as shown in Chemical formula 1 as long as it possesses the same physicochemical properties as the above-mentioned protein.

Chemical Formula 1 (SEQ ID NO: 4)

```
  1 Met—Thr—Ser—Lys—Gly—Pro—Glu—Glu—Glu—His—
 11 Pro—Ser—Val—Thr—Leu—Phe—Arg—Gin—Tyr—Leu—
 21 Arg—Ile—Arg—Thr—Val—Gln—Pro—Lys—Pro—Asp—
 31 Tyr—Gly—Ala—Ala—Val—Ala—Phe—Phe—Glu—Glu—
 41 Thr—Ala—Arg—Gin—Leu—Gly—Leu—Gly—Cys—Gln—
 51 Lys—Val—Glu—Val—Ala—Pro—Gly—Tyr—Val—Val—
 61 Thr—Val—Leu—Thr—Trp—Pro—Gly—Thr—Asn—Pro—
 71 Thr—Leu—Ser—Ser—Ile—Leu—Leu—Asn—Ser—His—
 81 Thr—Asp—Val—Val—Pro—Val—Phe—Lys—Glu—His—
 91 Trp—Ser—His—Asp—Pro—Phe—Glu—Ala—Phe—Lys—
101 Asp—Ser—Glu—Gly—Tyr—Ile—Tyr—Ala—Arg—Gly—
111 Ala—Gln—Asp—Met—Lys—Cys—Val—Ser—Ile—Gln—
121 Tyr—Leu—Glu—Ala—Val—Arg—Arg—Leu—Lys—Val—
131 Glu—Gly—His—Arg—Phe—Pro—Arg—Thr—Ile—His—
141 Met—Thr—Phe—Val—Pro—Asp—Glu—Glu—Val—Gly—
151 Gly—His—Gln—Gly—Met—Glu—Leu—Phe—Val—Gln—
161 Arg—Pro—Glu—Phe—His—Ala—Leu—Arg—Ala—Gly—
171 Phe—Ala—Leu—Asp—Glu—Gly—Ile—Ala—Asn—Pro—
181 Thr—Asp—Ala—Phe—Thr—Val—Phe—Tyr—Ser—Glu—
191 Arg—Ser—Pro—Trp—Trp—Val—Arg—Val—Thr—Ser—
201 Thr—Gly—Arg—Pro—Gly—His—Ala—Ser—Arg—Phe—
211 Met—Glu—Asp—Thr—Ala—Ala—Glu—Lys—Leu—His—
221 Lys—Val—Val—Asn—Ser—Ile—Leu—Ala—Phe—Arg—
231 Glu—Lys—Glu—Trp—Gln—Arg—Leu—Gln—Ser—Asn—
241 Pro—His—Leu—Lys—Glu—Gly—Ser—Val—Thr—Ser—
251 Val—Asn—Leu—Thr—Lys—Leu—Glu—Gly—Gly—Val—
261 Ala—Tyr—Asn—Val—Ile—Pro—Ala—Thr—Met—Ser—
271 Ala—Ser—Phe—Asp—Phe—Arg—Val—Ala—Pro—Asp—
281 Val—Asp—Phe—Lys—Ala—Phe—Glu—Glu—Gln—Leu—
291 Gln—Ser—Trp—Cys—Gln—Ala—Ala—Gly—Glu—Gly—
```

-continued
Chemical Formula 1 (SEQ ID NO: 4)

```
301 Val—Thr—Leu—Glu—Phe—Ala—Gln—Lys—Trp—Met—
311 His—Pro—Gln—Val—Thr—Pro—Thr—Asp—Asp—Ser—
321 Asn—Pro—Trp—Trp—Ala—Ala—Phe—Ser—Arg—Val—
331 Cys—Lys—Asp—Met—Asn—Leu—Thr—Leu—Glu—Pro—
341 Glu—Ile—Met—Pro—Ala—Ala—Thr—Asp—Asn—Arg—
351 Tyr—Ile—Arg—Ala—Val—Gly—Val—Pro—Ala—Leu—
361 Gly—Phe—Ser—Pro—Met—Asn—Arg—Thr—Pro—Val—
371 Leu—Leu—His—Asp—His—Asp—Glu—Arg—Leu—His—
381 Glu—Ala—Val—Phe—Leu—Arg—Gly—Val—Asp—Ile—
391 Tyr—Thr—Arg—Leu—Leu—Pro—Ala—Leu—Ala—Ser—
401 Val—Pro—Ala—Leu—Pro—Ser—Asp—Ser
```

Based on the above-mentioned amino acid sequence, the present inventors screened DNAs which might code the present protein from HPB-MLT cell, and found that the present protein contained the base sequence as shown in Chemical formula 2(SEQ ID NO: 3). The DNA according to the present invention is not restricted to that as shown in Chemical formula 2. The wording "substantially has the base sequence as shown in Chemical formula 2" as referred to in the invention means that it has the whole or a part of the base sequence of Chemical formula 2. The base sequences usable in the invention are, for example, those formed by a genetic code degeneracy wherein one or more bases in Chemical formula 2 are replaced with other bases, those which code the aforesaid homologous variants, and those which are complemental to the base sequence as shown in Chemical formula 2. The complementary base sequences may be wholly or partially complemental to that as shown in Chemical formula 2.

Chemical Formula 2 (SEQ ID NO: 3)

```
   1 ATG ACC AGC AAG GGT CCC GAG GAG GAG CAC
  31 CCA TCG GTG ACG CTC TTC CGC CAG TAC CTG
  61 CGT ATC CGC ACT GTC CAG CCC AAG CCT GAC
  91 TAT GGA GCT GCT GTG GCT TTC TTT GAG GAG
 121 ACA GCC CGC CAG CTG GGC CTG GGC TGT CAG
 151 AAA GTA GAG GTG GCA CCT GGC TAT GTG GTG
 181 ACC GTG TTG ACC TGG CCA GGC ACC AAC CCT
 211 ACA CTC TCC TCC ATC TTG CTC AAC TCC CAC
 241 ACG GAT GTG GTG CCT GTC TTC AAG GAA CAT
 271 TGG AGT CAC GAC CCC TTT GAG GCC TTC AAG
 301 GAT TCT GAG GGC TAC ATC TAT GCC AGG GGT
 331 GCC CAG GAC ATG AAG TGC GTC AGC ATC CAG
 361 TAC CTG GAA GCT GTG AGG AGG CTG AAG GTG
 391 GAG GGC CAC CGG TTC CCC AGA ACC ATC CAC
 421 ATG ACC TTT GTG CCT GAT GAG GAG GTT GGG
 451 GGT CAC CAA GGC ATG GAG CTG TTC GTG GAG
 481 CGG CCT GAG TTC CAC GCC CTG AGG GCA GGC
 511 TTT GCC CTG GAT GAG GGC ATA GCC AAT CCC
 541 ACT GAT GCC TTC ACT GTC TTT TAT AGT GAG
 571 CGG AGT CCC TGG TGG GTG CGG GTT ACC AGC
 601 ACT GGG AGG CCA GGC CAT GCC TCA CGC TTC
 631 ATG GAG GAC ACA GCA GCA GAG AAG CTG CAC
 661 AAG GTT GTA AAC TCC ATC CTG GCA TTC CGG
 691 GAG AAG GAA TGG CAG AGG CTG CAG TCA AAC
 721 CCC CAC CTG AAA GAG GGG TCC GTG ACC TCC
 751 GTG AAC CTG ACT AAG CTA GAG GGT GGC GTG
 781 GCC TAT AAC GTG ATA CCT GCC ACC ATG AGC
 811 GCC AGC TTT GAC TTC CGT GTG GCA CCG GAT
 841 GTG GAC TTC AAG GCT TTT GAG GAG CAG CTG
 871 CAG AGC TGG TGC CAG GCA GCT GGC GAG GGG
 901 GTC ACC CTA GAG TTT GCT CAG AAG TGG ATG
 931 CAC CCC CAA GTG ACA CCT ACT GAT GAC TCA
 961 AAC CCT TGG TGG GCA GCT TTT AGC CGG GTC
 991 TGC AAG GAT ATG AAC CTC ACT CTG GAG CCT
1021 GAG ATC ATG CCT GCT GCC ACT GAC AAC CGC
1051 TAT ATC CGC GCG GTG GGG GTC CCA GCT CTA
1081 GGC TTC TCA CCC ATG AAC CGC ACA CCT GTG
1111 CTG CTG CAC GAC CAC GAT GAA CGG CTG CAT
1141 GAG GCT GTG TTC CTC CGT GGG GTG GAC ATA
1171 TAT ACA CGC CTG CTG CCT GCC CTT GCC AGT
1201 GTG CCT GCC CTG CCC AGT GAC AGC
```

Furthermore, the present invention provides a process to prepare the above-mentioned protein, comprising culturing a cell "capable of producing said protein in a nutrient culture medium to form said protein, and recovering the resultant protein from the culture. Examples of such a cell are established cell lines derived from human T-cell leukemia such as HPB-MLT cell and MOLT-4 cell (ATCC CRL 1582), and not restricted to those of human origin. Similarly as the cells of human origin, cells of animal origin and microorganisms can be advantageously used in the invention as long as they can inherently produce the present protein, and those which had been introduced with the present DNA by conventional cell fusion or genetic engineering technique can be advantageously used in the invention as long as the present protein is recovered from their cultures.

The cells usable in the present process are not restricted to those described in the present specification, and, if necessary the present protein can be prepared by culturing any one of the cells in a nutrient culture medium while stimulating it with an adequate stimulant such as BCC and LPS, and recovering the resultant protein having a metastasis-inhibitory activity from the resultant cells or supernatant. The cultivation of such a cell is carried out according to conventional techniques for animal cells and microorganisms. Conventional nutrient culture media containing vitamins, minerals, carbohydrates and the like can be employed in the invention. The recovering methods suitably used in the invention are two or more methods usually used in the purification of physiologically-active proteinous substances: For example, salting out, dialysis, centrifugation, gel filtration chromatography, ion-exchange chromatography, affinity chromatography, electrophoresis, isoelectrofocusing and isoelectric fractionation are suitably used in combination.

The present invention attains the aforesaid object, and encompasses a novel protein possessing a metastasis-inhibitory activity, a DNA coding said protein, and the preparation of said protein.

The following experiments will explain the present invention.

EXPERIMENT 1

Assay for metastasis-inhibitory activity

In accordance with the method of Y. Naomoto et al. described in *Journal of Cancer Research and Clinical Oncology*, Vol.113, pp.544–549 (1987), a metastasis-inhibitory activity was assayed with a model wherein RPMI 4788 cells (FERM BP-2429) are transplanted to nude mice so as to induce lung metastasis.

In a test group, 5 or more BALB/c nude mice were injected through their tail veins with 0.2ml of phosphate buffer containing a test specimen 3 times in total before the cell transplantation, i.e. at 2 day, 1 day and 3 hours before the cell transplantation. From the next day of the transplantation of $2\times10^6$ RPMI 4788 cells per mouse, the mice were successively injected similarly as above with a test specimen one shot per day over a period of 7 days. In a control group, mice were similarly treated as in the test group except for using phosphate buffer free of the test specimen. On the 21st day after the cell transplantation, nude mice were sacrificed, and the number of metastatic nodules formed on the surfaces of the lungs was macroscopically counted. It was judged that a test specimen had a positive activity when the following requirements were fulfilled: (i) The mean value of numbers of lung metastatic nodules formed in the mice in the control group was 50 or more; (ii) the mean value of those in the test group was lowered to ½ or lower against that in the control group; and (iii) the reduction level in (ii) was evaluated as statistically significant.

EXPERIMENT 2

Preparation of supernatant from culture of HPB-MLT cell stimulated with BCG and LPS A new born hamster was first injected with a serum of anti-hamster thymus prepared from rabbits in usual manner, then subcutaneously transplanted with HPB-MLT cells, and bred for 4 weeks in usual manner. About 20 g weight tumor subcutaneously formed in the hamster was cut into pieces, dispersed, washed with serum-free RPMI 1640 medium, and suspended in a fresh preparation of the same medium to give a concentration of $5\times10^6$ cells/ml. The cell suspension was added with 10 μg/ml BCG and incubated at 37° C. for one day. Thereafter, the resultant cell suspension was added with one μg/ml LPS, incubated for one day, and centrifuged to obtain a supernatant.

EXPERIMENT 3

Purification and physicochemical properties of the present protein

The supernatant in Experiment 2 was concentrated by about 20-fold on "AIL 3013", a membrane module commercialized by Asahi Chemical Ind., Tokyo, Japan, and the concentrate was dialyzed against 25 mM imidazol-HCl buffer (pH 7.4). The resultant solution in a dialytic bag was fed to a column packed with "PBE-94", a product of Pharmacia LKB, Uppsala, Sweden, preequilibrated with 25 mM imidazol-HCl buffer (pH 7.4). The column was fed with "Polybuffer® 74 (pH 4.0)", commercialized by Pharmacia LKB, Uppsala, Sweden, to fractionate the supernatant, and the resultant fractions were respectively dialyzed against phosphate-buffered saline (PBS), followed by assaying each fraction for cancer metastasis-inhibitory activity. As a result, it was revealed that the fractions eluted between a pH range of 5.0–6.5 had cancer metastasis-inhibitory activity. The active fractions were pooled, and refractionated on a column packed with "Sephacryl S-200", a product commercialized by Pharmacia LKB Uppsala, Sweden. The resultant fractions were assayed for their cancer metastasis-inhibitory activity to test whether or not that the fractions, eluted with a ratio of (Elution volume)/(Void volume) in the range of 0.5–0.65, might have the activity. The active fractions were pooled and dialyzed against 10 mM potassium phosphate buffer (pH 7.4). The solution in a dialytic bag was fed to a column packed with "DEAE-SPW", a product of Tosoh Corporation, Tokyo, Japan, preequilibrated with 10 mM potassium phosphate buffer (pH 7.4), and eluted with a liner gradient of 10–500 mM potassium phosphate buffer (pH 7.4). In this case, a substance with cancer metastasis-inhibitory activity was eluted in fractions with about 70 mM potassium phosphate. The fractions thus obtained were pooled and dialyzed against 10 mM sodium phosphate buffer (pH 6.8), and fed to a hydroxyapatite column commercialized by Toa Nenryo Kogyo K.K., Tokyo, Japan, preequilibrated with 10 mM sodium phosphate buffer (pH 6.8). In this case, cancer metastasis-inhibitory activity was found in non-adsorbed fractions which were then fed to a column packed with "Mono-P", a product of Pharmacia LKB, Upssala, Sweden, preequilibrated with 25 mM bis-tris-iminodiacetate buffer (pH 7.1), and eluted with "Polybuffer® 74 (pH 4.0)", a product of Pharmacia LKB, Uppsala, Sweden, followed by isolating the present protein with cancer metastasis-inhibitory activity. Thus, about 70 μg of the present protein was isolated from 50L of the culture supernatant of HPB-MLT cells stimulated with BCG and LPS. The physicochemical properties of the present protein were studied with the isolated protein.

(1) Molecular weight

In accordance with the method of U. K. Laemmli described in *Nature*, Vol.227, pp.680–685 (1970), the protein was subjected to sodium dodecyl sulfate polyacrylamide gel electrophoresis (abbreviated as "SDS-PAGE" hereinafter), and the molecular weight was determined to be 45,000±5,000 based on the relative mobility of the protein against marker proteins.

(2) Isoelectric point

The isoelectric point of the protein was estimated to be 5.7±0.5 based on the pHs of eluates on a column chromatography using Mono-P column;

(3) Partial amino acid sequence

The protein was subjected to SDS-PAGE, and a band corresponding to the molecular weight of about 45,000 in the resultant gel was isolated by cutting. The resultant gel piece was soaked in 100 mM Tris-HCl buffer (pH 9.0) containing 0.1% sodium dodecyl sulfate (SDS) at 37° C. for one hour, and digested at 37° C. overnight by the addition of 5 μg/ml lysyl endopeptidase, an enzyme specimen commercialized by Wako Pure Chemical Industries, Ltd., Tokyo, Japan. The supernatant obtained from the resultant was fractionated on a reverse-phase chromatography using a column of "C-18", commercialized by VYDAC, Hesperia, USA, equipped with a precolumn of DEAE, followed by recovering peptide fragments which were then analyzed on "470A", an amino acid sequencer commercialized by Applied Biosystems Inc., Foster City, USA. The results were as shown in Chemical formulas 3, 4, 5 and 6.

Chemical formula 3 (SEQ ID NO: 1) Asp-Ser-Glu-Gly-Tyr-Ile-Tyr-Ala-Arg-Gly-Ala-Gln-Asp-Met-Lys Chemical formula 4 (SEQ ID NO: 2) Glu-His-Trp-Ser-His-Asp-Pro-Phe-Glu Chemical formula 5 (SEQ ID NO Glu-Trp-Gln-Arg-Leu-Gtn-Ser-Asn-Pro-His-Leu-Lys Chemical formula 6 Leu-Glu-Gly-Gly-Val-Ala-Tyr-Asn-Val-Ile-Pro (4) Solubility in solvent The protein was soluble in water, physiological saline and phosphate buffer.

(5) Biological activity

The protein was tested for cancer metastasis-inhibitory activity with the method in Experiment 1. As a result, the number of metastatic nodules was 314±169 in a control group consisting of 5 nude mice, while that in a test group, wherein 5 nude mice were administered with a solution containing 250 μg/ml of the protein, was 100±43. These confirmed that the protein exhibited a strong cancer metastasis-inhibitory activity.

(6) Stability

The protein was dissolved in phosphate buffer (pH 7.2) and allowed to stand at 100° C. for 30 minutes, followed by determining the residual activity with the method in Experiment 1 to give no activity. Thus, it was revealed that the protein was inactivated under the conditions.

While the protein was treated by dissolving it in phosphate buffer (pH 7.2), and allowing the resultant solution to stand at 4° C. for one month, followed by assaying the residual activity similarly as above. As a result, no substantial loss of activity was found, and this revealed that the protein was stable under the conditions.

EXPERIMENT 4

Acute toxicity

By using 7 week-old mice, the present protein was tested for acute toxicity. As a result, the LD50 in mice of the protein was 50 mg/kg or higher when intravenously administered to the mice, and this revealed that the toxicity was extremely low.

Experiment 5

Base sequence coding the present protein

In this experiment, the base sequence of the present protein was determined by conventional method as described by T. Maniatis et al. in *Molecular Cloning, A Laboratory Manual,* 2nd edition, published by Cold Spring Harbor LaboratoryPress (1989), New York, USA.

Experiment 5-1

Construction of cDNA library of HPB-MLT cell

HPB-MLT cells obtained by the method in Experiment 2 were suspended in a serum-free RPMI 1640 medium to give a concentration of $5 \times 10^6$ cells/ml. The cell suspension was added with 10 μg/ml BCG and incubated at 37° C. for one day. The culture thus obtained was added with one g/ml LPS and incubated for 4.5 hours. The resultant culture was centrifuged to obtain cells which were then solubilized with 4M guanidium isocyanate and homogenized. The resultant homogenate was overlaid on 5.7M cesium chloride, and the mixture was centrifuged at 25,000 rpm for 17 hours to obtain the whole RNAs of the cells. Poly (A)$^+$ RNA was purified from the whole RNAs on "Oligotex"-dT30<Super>", a bead for purification of poly (A)$^+$ RNA commercialized by Daiichi Pure Chemicals, Tokyo, Japan. The purified poly (A)$^+$ RNA was treated with "cDNA synthesis system plus", a product of Amersham International plc, Buckinghashire, England, to synthesize a cDNA under the direction of the appended manual. The cDNA thus obtained was ligated with a λgt10 phage DNA by using "cDNA cloning system λgt10", a product of Amersham International plc, Buckinghashire, Englnad. The resultant recombinant phage DNA was packaged by "Lambda(λ) in vitro packaging kit", a product of Amersham International plc, Buckinghashire, England, to obtain a cDNA library of HPB-MLT cell.

Experiment 5-2

Construction of radiolabeled DNA probe

Based on the partial amino acid sequence as shown in Chemical formula 3 in Experiment 3, base sequences estimable from the amino acid sequence of Glu-Gly-Tyr-Ile-Tyr-Ala (SEQ ID NO: 7) in Chemical formula 3 were synthesized by a DNA synthesizer commercialized by Applied Biosystems, Inc., Foster City, USA. Ninety-six base sequences consisting of 17 synthesized bases are as shown in Table 1.

TABLE 1

| Probe 1: | GAG | GGG | TAT | ATA | TAT | GC (SEQ ID NO: 8) |
|---|---|---|---|---|---|---|
| | A | A | C | T | C | |
| | | T | | C | | |
| | | C | | | | |

As for the partial amino acid sequence as shown in Chemical formula 5, complementary chains of base sequences, estimable from Asn-Pro-His-Leu-Lys (SEQ ID NO:9) in the partial amino acid sequence in Chemical formula 5, were synthesized similarly as above. Ninety-six base sequences consisting of 14 synthesized bases are as shown in Table 2. The DNAs thus obtained were radiolabeled with [γ-$^{32}$P]ATP and T4 polynucleotide kinase.

TABLE 2

| Probe 2: | TTG | AGG | TGG | GGG | TT (SEQ ID NO: 10) |
|---|---|---|---|---|---|
| | A | A | A | A | |
| | T | | T | | |
| | C | | C | | |
| | TTT | AAG | TGG | GGG | TT |
| | C | A | A | A | |
| | | | T | | |
| | | | C | | |

Experiment 5-3

Screening with radiolabeled DNA probes

A solution of the recombinant λgt10, a cDNA library of HPB-MLT cell prepared in Experiment 5-1, was mixed with an overnight culture of microorganisms of *E. coli* strain NM 514 in L-broth, and the mixture was incubated at 37° C. for 15 minutes. The resultant was admixed with a soft agar, and the resultant mixture was overlaid on a hard-agar plate and solidified. The resultant agar plate containing the microorganisms were incubated at 37° C. for 8 hours, cooled and overlaid with "Hybond-N filter", a membrane filter of Amersham International plc, Buckinghamshire, England, to transfer the phage and to fix the phage DNA on the membrane filter. In order to prevent a non-specific bonding of the radiolabeled DNA probes with DNAs except for the objective complementary DNA, the membrane filter was soaked in a solution of a salmon sperm DNA commercialized by Sigma Chemical company, St., Louis, USA, to effect pre-hybridization, followed by screening positive clones by the southern hybridization with the radiolabeled DNA probes in Experiment 5-2. The results in the first screening test with the probe 1 in Table 1 and the second screening test with the probe 2 in Table 2 revealed that 3 positive clones were present among about 600,000 clones. Phage DNAs isolated from the positive clones were digested with a restriction enzyme EcoRI to remove them from vector DNAs, and the length of the inserted fragments were studied on agarose electrophoresis, followed by analyzing a clone having the longest inserted-fragment of about 1.5 kbp.

Experiment 5-4

Base sequence of gene coding the present protein

From the positive clones obtained in Experiment 5-3, a phage DNA was isolated and digested with a restriction enzyme EcoRI, and the resultant fragments were separated on SDS-PAGE to obtain an inserted DNA fragment of about 1.5 kbp which was then ligated with a pUC18 plasmid with a ligation kit commercialized by Amersham International plc, Buckinghashire, England, to obtain a recombinant plasmid. The recombinant plasmid thus obtained was introduced in usual manner into *E. coli* to obtain a recombinant microorganism, and from which a plasmid DNA was prepared. The dideoxy chain termination method was applied to the resultant plasmid DNA to reveal the base sequence of the present protein. Based on the base sequence, the amino acid sequence of the present protein was estimated. As a result, it was revealed that the present DNA consisted of 1,224 bases and coded a protein consisting of 408 amino acids. The estimated amino acid sequence encompassed the amino acid sequences as shown in Chemical formulas 3, 4, 5 and 6 in Experiment 3.

The following is an example of the preparation of the present protein.

EXAMPLE

Similarly as the method in Experiment 2, MOLT-4 cell (ATCC CRL 1582), an established cell line derived from human T-cell leukemia commercialized by Dainippon Pharmaceutical Co., Ltd., Tokyo, Japan, were cultured in a nutrient culture medium while stimulating the cells with BCG and LPS. Similarly as in Experiment 3, a supernatant prepared from the resultant culture was treated to obtain the present protein possessing cancer metastasis-inhibitory activity. The yield was about 40 µg per 50L of the culture supernatant. The protein had the same physicochemical properties as the one in Experiment 3.

The protein according to the present invention effectively inhibits the metastasis of cancers, and this renders it advantageously useful as prophylactic-, therapeutic- and diagnostic-agents for cancer metastases. The toxicity of the present protein is satisfactorily low, because of this it can be systematically administered to patients in the form of an injection, sublingual agent, and the like.

The present protein having the aforesaid advantages is prepared in an industrial scale by the present preparation.

The DNA coding the present protein is useful in the preparation of the present protein by genetic engineering techniques.

While there has been described what is at present considered to be the preferred embodiments of the invention, it will be understood the various modifications may be made therein, and it is intended to cover the appended claims all such modifications, as fall within the true spirits and scope of the invention.

We claim:

1. A DNA which encodes a protein having the following physicochemial properties:

(1) Molecular weight
45,000±5,000;
Isoelectric point
pI=5.7±0.5;
(3) Partial amino acid sequence
Possessing a partial amino acid sequence of Asp-Ser-Glu-Gly-Tyr-Ile-Tyr-Ala-Arg-Gly-Ala-Gln-Asp-Met-Lys (SEQ ID NO:1) or Glu-His-Trp-Ser-His-Asp-Pro-Phe-Glu (SEQ ID NO:2);

(4) Solubility in solvent

Soluble in water, physiological saline and phosphate buffer;

(5) Biological activity

Exhibiting metastasis-inhibitory activity on RPMI 4788 cell (FERM BP -2429), an established cell line derived from human colon cancer; and (6) Stability Inactivated in water at pH 7.2 and 100° C. for 30 minutes Stable in water at pH 7.2 and 4° C. for one month.

(7) Acute toxicity

Exhibiting an $LD_{50}$ of 50 mg/kg or higher in mouse when intravenously administered to the mouse.

2. The DNA of claim 1, which has the following base sequence as shown in Chemical formula 2(SEQ ID NO:3).

Chemical Formula 2

1 ATG ACC AGC AAG GGT CCC GAG GAG GAG CAC
31 CCA TCG GTG ACG CTC TTC CGC CAG TAC CTG
61 CGT ATC CGC ACT GTC CAG CCC AAG CCT GAC
91 TAT GGA GCT GCT GTG GCT TTC TTT GAG GAG
121 ACA GCC CGC CAG CTG GGC CTG GGC TGT CAG
151 AAA GTA GAG GTG GCA CCT GGC TAT GTG GTG
181 ACC GTG TTG ACC TGG CCA GGC ACC AAC CCT
211 ACA CTC TCC TCC ATC TTG CTC AAC TCC CAC
241 ACG GAT GTG GTG CCT GTC TTC AAG GAA CAT
271 TGG AGT CAC GAC CCC TTT GAG GCC TTC AAG
301 GAT TCT GAG GGC TAC ATC TAT GCC AGG GGT
331 GCC CAG GAC ATG AAG TGC GTC AGC ATC CAG
361 TAC CTG GAA GCT GTG AGG AGG CTG AAG GTG
391 GAG GGC CAC CGG TTC CCC AGA ACC ATC CAC
421 ATG ACC TTT GTG CCT GAT GAG GAG GTT GGG
451 GGT CAC CAA GGC ATG GAG CTG TTC GTG CAG
481 CGG CCT GAG TTC CAC GCC CTG AGG GCA GGC
511 TTT GCC CTG GAT GAG GGC ATA GCC AAT CCC
541 ACT GAT GCC TTC ACT GTC TTT TAT AGT GAG

-continued

Chemical Formula 2

571 CGG AGT CCC TGG TGG GTG CGG GTT ACC AGC
601 ACT GGG AGG CCA GGC CAT GCC TCA CGC TTC
631 ATG GAG GAC ACA GCA GCA GAG AAG CTG CAC
661 AAG GTT GTA AAC TCC ATC CTG GCA TTC CGG
691 GAG AAG GAA TGG CAG AGG CTG CAG TCA AAC
721 CCC CAC CTG AAA GAG GGG TCC GTG ACC TCC
751 GTG AAC CTG ACT AAG CTA GAG GGT GGC GTG
781 GCC TAT AAC GTG ATA CCT GCC ACC ATG AGC
811 GCC AGC TTT GAC TTC CGT GTG GCA CCG GAT
841 GTG GAC TTC AAG GCT TTT GAG GAG CAG CTG
871 CAG AGC TGG TGC CAG GCA GCT GGC GAG GGG
901 GTC ACC CTA GAG TTT GCT CAG AAG TGG ATG
931 CAC CCC CAA GTG ACA CCT ACT GAT GAC TCA
961 AAC CCT TGG TGG GCA GCT TTT AGC CGG GTC
991 TGC AAG GAT ATG AAC CTC ACT CTG GAG CCT
1021 GAG ATC ATG CCT GCT GCC ACT GAC AAC CGC
1051 TAT ATC CGC GCG GTG GGG GTC CCA GCT CTA
1081 GGC TTC TCA CCC ATG AAC CGC ACA CCT GTG
1111 CTG CTG CAC GAC CAC GAT GAA CGG CTG CAT
1141 GAG GCT GTG TTC CTC CGT GGG GTG GAC ATA
1171 TAT ACA CGC CTG CTG CCT GCC CTT GCC AGT
1201 GTG CCT GCC CTG CCC AGT GAC AGC.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
         ( A ) LENGTH: 15 amino acids
         ( B ) TYPE: amino acid
         ( C ) STRANDEDNESS: single
         ( D ) TOPOLOGY: linear ( i i ) MOLECULE TYPE: peptide ( x i ) SEQUENCE DESCRIPTION: SEQ ID NO:1:

Asp Ser Glu Gly Tyr Ile Tyr Ala Arg Gly Ala Gln Asp Met Lys
   1               5                   10                  15

( 2 ) INFORMATION FOR SEQ ID NO:2:

( i ) SEQUENCE CHARACTERISTICS:
         ( A ) LENGTH: 9 amino acids
         ( B ) TYPE: amino acid
         ( C ) STRANDEDNESS: single
         ( D ) TOPOLOGY: linear ( i i ) MOLECULE TYPE: peptide ( x i ) SEQUENCE DESCRIPTION: SEQ ID NO:2:

Glu His Trp Ser His Asp Pro Phe Glu
   1               5

( 2 ) INFORMATION FOR SEQ ID NO:3:

( i ) SEQUENCE CHARACTERISTICS:
         ( A ) LENGTH: 1224 base pairs
         ( B ) TYPE: nucleic acid
         ( C ) STRANDEDNESS: single
         ( D ) TOPOLOGY: linear ( i i ) MOLECULE TYPE: cDNA ( i x ) FEATURE:
         ( A ) NAME/KEY: CDS
         ( B ) LOCATION: 1..1224

( x i ) SEQUENCE DESCRIPTION: SEQ ID NO:3:

| | | | | | | | | | | | | | | | | |
|---|---|---|---|---|---|---|---|---|---|---|---|---|---|---|---|---|
| ATG | ACC | AGC | AAG | GGT | CCC | GAG | GAG | GAG | CAC | CCA | TCG | GTG | ACG | CTC | TTC | 48 |
| Met 1 | Thr | Ser | Lys | Gly 5 | Pro | Glu | Glu | Glu | His 10 | Pro | Ser | Val | Thr | Leu 15 | Phe | |
| CGC | CAG | TAC | CTG | CGT | ATC | CGC | ACT | GTC | CAG | CCC | AAG | CCT | GAC | TAT | GGA | 96 |
| Arg | Gln | Tyr | Leu 20 | Arg | Ile | Arg | Thr | Val 25 | Gln | Pro | Lys | Pro | Asp 30 | Tyr | Gly | |
| GCT | GCT | GTG | GCT | TTC | TTT | GAG | GAG | ACA | GCC | CGC | CAG | CTG | GGC | CTG | GGC | 144 |
| Ala | Ala | Val 35 | Ala | Phe | Phe | Glu | Glu 40 | Thr | Ala | Arg | Gln | Leu 45 | Gly | Leu | Gly | |
| TGT | CAG | AAA | GTA | GAG | GTG | GCA | CCT | GGC | TAT | GTG | GTG | ACC | GTG | TTG | ACC | 192 |
| Cys | Gln 50 | Lys | Val | Glu | Val | Ala 55 | Pro | Gly | Tyr | Val | Val 60 | Thr | Val | Leu | Thr | |
| TGG | CCA | GGC | ACC | AAC | CCT | ACA | CTC | TCC | TCC | ATC | TTG | CTC | AAC | TCC | CAC | 240 |
| Trp 65 | Pro | Gly | Thr | Asn | Pro 70 | Thr | Leu | Ser | Ser | Ile 75 | Leu | Leu | Asn | Ser | His 80 | |
| ACG | GAT | GTG | GTG | CCT | GTC | TTC | AAG | GAA | CAT | TGG | AGT | CAC | GAC | CCC | TTT | 288 |
| Thr | Asp | Val | Val | Pro 85 | Val | Phe | Lys | Glu | His 90 | Trp | Ser | His | Asp | Pro 95 | Phe | |
| GAG | GCC | TTC | AAG | GAT | TCT | GAG | GGC | TAC | ATC | TAT | GCC | AGG | GGT | GCC | CAG | 336 |
| Glu | Ala | Phe | Lys 100 | Asp | Ser | Glu | Gly | Tyr 105 | Ile | Tyr | Ala | Arg | Gly 110 | Ala | Gln | |
| GAC | ATG | AAG | TGC | GTC | AGC | ATC | CAG | TAC | CTG | GAA | GCT | GTG | AGG | AGG | CTG | 384 |
| Asp | Met | Lys 115 | Cys | Val | Ser | Ile | Gln 120 | Tyr | Leu | Glu | Ala | Val 125 | Arg | Arg | Leu | |
| AAG | GTG | GAG | GGC | CAC | CGG | TTC | CCC | AGA | ACC | ATC | CAC | ATG | ACC | TTT | GTG | 432 |
| Lys | Val 130 | Glu | Gly | His | Arg | Phe 135 | Pro | Arg | Thr | Ile | His 140 | Met | Thr | Phe | Val | |
| CCT | GAT | GAG | GAG | GTT | GGG | GGT | CAC | CAA | GGC | ATG | GAG | CTG | TTC | GTG | CAG | 480 |
| Pro 145 | Asp | Glu | Glu | Val | Gly 150 | Gly | His | Gln | Gly | Met 155 | Glu | Leu | Phe | Val | Gln 160 | |
| CGG | CCT | GAG | TTC | CAC | GCC | CTG | AGG | GCA | GGC | TTT | GCC | CTG | GAT | GAG | GGC | 528 |
| Arg | Pro | Glu | Phe | His 165 | Ala | Leu | Arg | Ala | Gly 170 | Phe | Ala | Leu | Asp | Glu 175 | Gly | |
| ATA | GCC | AAT | CCC | ACT | GAT | GCC | TTC | ACT | GTC | TTT | TAT | AGT | GAG | CGG | AGT | 576 |
| Ile | Ala | Asn | Pro 180 | Thr | Asp | Ala | Phe | Thr 185 | Val | Phe | Tyr | Ser | Glu 190 | Arg | Ser | |
| CCC | TGG | TGG | GTG | CGG | GTT | ACC | AGC | ACT | GGG | AGG | CCA | GGC | CAT | GCC | TCA | 624 |
| Pro | Trp | Trp 195 | Val | Arg | Val | Thr | Ser 200 | Thr | Gly | Arg | Pro | Gly 205 | His | Ala | Ser | |
| CGC | TTC | ATG | GAG | GAC | ACA | GCA | GCA | GAG | AAG | CTG | CAC | AAG | GTT | GTA | AAC | 672 |
| Arg | Phe | Met 210 | Glu | Asp | Thr | Ala | Ala 215 | Ala | Glu | Lys | Leu | His 220 | Lys | Val | Val | Asn | |
| TCC | ATC | CTG | GCA | TTC | CGG | GAG | AAG | GAA | TGG | CAG | AGG | CTG | CAG | TCA | AAC | 720 |
| Ser | Ile | Leu 225 | Ala | Phe | Arg 230 | Glu | Lys | Glu | Trp | Gln 235 | Arg | Leu | Gln | Ser | Asn 240 | |
| CCC | CAC | CTG | AAA | GAG | GGG | TCC | GTG | ACC | TCC | GTG | AAC | CTG | ACT | AAG | CTA | 768 |
| Pro | His | Leu | Lys | Glu 245 | Gly | Ser | Val | Thr | Ser 250 | Val | Asn | Leu | Thr | Lys 255 | Leu | |
| GAG | GGT | GGC | GTG | GCC | TAT | AAC | GTG | ATA | CCT | GCC | ACC | ATG | AGC | GCC | AGC | 816 |
| Glu | Gly | Gly | Val | Ala 260 | Tyr | Asn | Val | Ile | Pro 265 | Ala | Thr | Met | Ser | Ala 270 | Ser | |
| TTT | GAC | TTC | CGT | GTG | GCA | CCG | GAT | GTG | GAC | TTC | AAG | GCT | TTT | GAG | GAG | 864 |
| Phe | Asp | Phe | Arg 275 | Val | Ala | Pro | Asp | Val 280 | Asp | Phe | Lys | Ala | Phe 285 | Glu | Glu | |
| CAG | CTG | CAG | AGC | TGG | TGC | CAG | GCA | GCT | GGC | GAG | GGG | GTC | ACC | CTA | GAG | 912 |
| Gln | Leu | Gln 290 | Ser | Trp | Cys | Gln | Ala 295 | Ala | Gly | Glu | Gly | Val 300 | Thr | Leu | Glu | |
| TTT | GCT | CAG | AAG | TGG | ATG | CAC | CCC | CAA | GTG | ACA | CCT | ACT | GAT | GAC | TCA | 960 |
| Phe | Ala | Gln | Lys | Trp 310 | Met | His | Pro | Gln | Val 315 | Thr | Pro | Thr | Asp | Asp 320 | Ser | |

| | | | | | | | | | | | | | | | | |
|---|---|---|---|---|---|---|---|---|---|---|---|---|---|---|---|---|
| AAC | CCT | TGG | TGG | GCA | GCT | TTT | AGC | CGG | GTC | TGC | AAG | GAT | ATG | AAC | CTC | 1008 |
| Asn | Pro | Trp | Trp | Ala | Ala | Phe | Ser | Arg | Val | Cys | Lys | Asp | Met | Asn | Leu | |
| | | | 325 | | | | | 330 | | | | | 335 | | | |
| ACT | CTG | GAG | CCT | GAG | ATC | ATG | CCT | GCT | GCC | ACT | GAC | AAC | CGC | TAT | ATC | 1056 |
| Thr | Leu | Glu | Pro | Glu | Ile | Met | Pro | Ala | Ala | Thr | Asp | Asn | Arg | Tyr | Ile | |
| | | | 340 | | | | | 345 | | | | | 350 | | | |
| CGC | GCG | GTG | GGG | GTC | CCA | GCT | CTA | GGC | TTC | TCA | CCC | ATG | AAC | CGC | ACA | 1104 |
| Arg | Ala | Val | Gly | Val | Pro | Ala | Leu | Gly | Phe | Ser | Pro | Met | Asn | Arg | Thr | |
| | | 355 | | | | | 360 | | | | | 365 | | | | |
| CCT | GTG | CTG | CTG | CAC | GAC | CAC | GAT | GAA | CGG | CTG | CAT | GAG | GCT | GTG | TTC | 1152 |
| Pro | Val | Leu | Leu | His | Asp | His | Asp | Glu | Arg | Leu | His | Glu | Ala | Val | Phe | |
| | 370 | | | | | 375 | | | | | 380 | | | | | |
| CTC | CGT | GGG | GTG | GAC | ATA | TAT | ACA | CGC | CTG | CTG | CCT | GCC | CTT | GCC | AGT | 1200 |
| Leu | Arg | Gly | Val | Asp | Ile | Tyr | Thr | Arg | Leu | Leu | Pro | Ala | Leu | Ala | Ser | |
| 385 | | | | | 390 | | | | | 395 | | | | | 400 | |
| GTG | CCT | GCC | CTG | CCC | AGT | GAC | AGC | | | | | | | | | 1224 |
| Val | Pro | Ala | Leu | Pro | Ser | Asp | Ser | | | | | | | | | |
| | | | | 405 | | | | | | | | | | | | |

(2) INFORMATION FOR SEQ ID NO:4:

(i) SEQUENCE CHARACTERISTICS:
        (A) LENGTH: 408 amino acids
        (B) TYPE: amino acid
        (D) TOPOLOGY: linear (ii) MOLECULE TYPE: protein (xi) SEQUENCE DESCRIPTION: SEQ ID NO:4:

| | | | | | | | | | | | | | | | |
|---|---|---|---|---|---|---|---|---|---|---|---|---|---|---|---|
| Met | Thr | Ser | Lys | Gly | Pro | Glu | Glu | Glu | His | Pro | Ser | Val | Thr | Leu | Phe |
| 1 | | | | 5 | | | | | 10 | | | | | 15 | |
| Arg | Gln | Tyr | Leu | Arg | Ile | Arg | Thr | Val | Gln | Pro | Lys | Pro | Asp | Tyr | Gly |
| | | | 20 | | | | | 25 | | | | | 30 | | |
| Ala | Ala | Val | Ala | Phe | Phe | Glu | Glu | Thr | Ala | Arg | Gln | Leu | Gly | Leu | Gly |
| | | | 35 | | | | | 40 | | | | | 45 | | |
| Cys | Gln | Lys | Val | Glu | Val | Ala | Pro | Gly | Tyr | Val | Val | Thr | Val | Leu | Thr |
| | 50 | | | | | 55 | | | | | 60 | | | | |
| Trp | Pro | Gly | Thr | Asn | Pro | Thr | Leu | Ser | Ser | Ile | Leu | Leu | Asn | Ser | His |
| 65 | | | | | 70 | | | | 75 | | | | | | 80 |
| Thr | Asp | Val | Val | Pro | Val | Phe | Lys | Glu | His | Trp | Ser | His | Asp | Pro | Phe |
| | | | | 85 | | | | | 90 | | | | | 95 | |
| Glu | Ala | Phe | Lys | Asp | Ser | Glu | Gly | Tyr | Ile | Tyr | Ala | Arg | Gly | Ala | Gln |
| | | | 100 | | | | | 105 | | | | | 110 | | |
| Asp | Met | Lys | Cys | Val | Ser | Ile | Gln | Tyr | Leu | Glu | Ala | Val | Arg | Arg | Leu |
| | | 115 | | | | | 120 | | | | | 125 | | | |
| Lys | Val | Glu | Gly | His | Arg | Phe | Pro | Arg | Thr | Ile | His | Met | Thr | Phe | Val |
| | 130 | | | | | 135 | | | | | 140 | | | | |
| Pro | Asp | Glu | Glu | Val | Gly | Gly | His | Gln | Gly | Met | Glu | Leu | Phe | Val | Gln |
| 145 | | | | | 150 | | | | | 155 | | | | | 160 |
| Arg | Pro | Glu | Phe | His | Ala | Leu | Arg | Ala | Gly | Phe | Ala | Leu | Asp | Glu | Gly |
| | | | | 165 | | | | | 170 | | | | | 175 | |
| Ile | Ala | Asn | Pro | Thr | Asp | Ala | Phe | Thr | Val | Phe | Tyr | Ser | Glu | Arg | Ser |
| | | | 180 | | | | | 185 | | | | | 190 | | |
| Pro | Trp | Trp | Val | Arg | Val | Thr | Ser | Thr | Gly | Arg | Pro | Gly | His | Ala | Ser |
| | | | 195 | | | | | 200 | | | | | 205 | | |
| Arg | Phe | Met | Glu | Asp | Thr | Ala | Ala | Glu | Lys | Leu | His | Lys | Val | Val | Asn |
| | | 210 | | | | | 215 | | | | | 220 | | | |
| Ser | Ile | Leu | Ala | Phe | Arg | Glu | Lys | Glu | Trp | Gln | Arg | Leu | Gln | Ser | Asn |

|     |     |     |     | 225 |     |     |     |     | 230 |     |     |     |     | 235 |     |     |     |     | 240 |
| --- | --- | --- | --- | --- | --- | --- | --- | --- | --- | --- | --- | --- | --- | --- | --- | --- | --- | --- | --- |
| Pro | His | Leu | Lys | Glu | Gly | Ser | Val | Thr | Ser | Val | Asn | Leu | Thr | Lys | Leu |
|     |     |     |     | 245 |     |     |     |     | 250 |     |     |     |     | 255 |     |
| Glu | Gly | Gly | Val | Ala | Tyr | Asn | Val | Ile | Pro | Ala | Thr | Met | Ser | Ala | Ser |
|     |     |     |     | 260 |     |     |     |     | 265 |     |     |     |     | 270 |     |
| Phe | Asp | Phe | Arg | Val | Ala | Pro | Asp | Val | Asp | Phe | Lys | Ala | Phe | Glu | Glu |
|     |     |     | 275 |     |     |     |     | 280 |     |     |     |     | 285 |     |     |
| Gln | Leu | Gln | Ser | Trp | Cys | Gln | Ala | Ala | Gly | Glu | Gly | Val | Thr | Leu | Glu |
|     |     | 290 |     |     |     | 295 |     |     |     |     | 300 |     |     |     |     |
| Phe | Ala | Gln | Lys | Trp | Met | His | Pro | Gln | Val | Thr | Pro | Thr | Asp | Asp | Ser |
| 305 |     |     |     |     | 310 |     |     |     |     | 315 |     |     |     |     | 320 |
| Asn | Pro | Trp | Trp | Ala | Ala | Phe | Ser | Arg | Val | Cys | Lys | Asp | Met | Asn | Leu |
|     |     |     |     | 325 |     |     |     |     | 330 |     |     |     |     | 335 |     |
| Thr | Leu | Glu | Pro | Glu | Ile | Met | Pro | Ala | Ala | Thr | Asp | Asn | Arg | Tyr | Ile |
|     |     |     | 340 |     |     |     |     | 345 |     |     |     |     | 350 |     |     |
| Arg | Ala | Val | Gly | Val | Pro | Ala | Leu | Gly | Phe | Ser | Pro | Met | Asn | Arg | Thr |
|     |     | 355 |     |     |     |     | 360 |     |     |     |     | 365 |     |     |     |
| Pro | Val | Leu | Leu | His | Asp | His | Asp | Glu | Arg | Leu | His | Glu | Ala | Val | Phe |
|     | 370 |     |     |     |     | 375 |     |     |     |     | 380 |     |     |     |     |
| Leu | Arg | Gly | Val | Asp | Ile | Tyr | Thr | Arg | Leu | Leu | Pro | Ala | Leu | Ala | Ser |
| 385 |     |     |     |     | 390 |     |     |     |     | 395 |     |     |     |     | 400 |
| Val | Pro | Ala | Leu | Pro | Ser | Asp | Ser |
|     |     |     |     | 405 |     |     |     |

( 2 ) INFORMATION FOR SEQ ID NO:5:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

| Glu | Trp | Gln | Arg | Leu | Gln | Ser | Asn | Pro | His | Leu | Lys |
| --- | --- | --- | --- | --- | --- | --- | --- | --- | --- | --- | --- |
| 1   |     |     |     | 5   |     |     |     |     | 10  |     |     |

( 2 ) INFORMATION FOR SEQ ID NO:6:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

| Leu | Glu | Gly | Gly | Val | Ala | Tyr | Asn | Val | Ile | Pro |
| --- | --- | --- | --- | --- | --- | --- | --- | --- | --- | --- |
| 1   |     |     |     | 5   |     |     |     |     | 10  |     |

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
      Glu  Gly  Tyr  Ile  Tyr  Ala
      1               5
```

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

```
GAGGGGTATA  TATATGC                                                17
```

( 2 ) INFORMATION FOR SEQ ID NO:9:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
      Asn  Pro  His  Leu  Lys
      1               5
```

( 2 ) INFORMATION FOR SEQ ID NO:10:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

```
TTGAGGTGGG  GGTT                                                   14
```

( 2 ) INFORMATION FOR SEQ ID NO:11:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

```
TTTAAGTGGG  GGTT                                                   14
```